(12) United States Patent
Izuchukwu et al.

(10) Patent No.: US 6,513,523 B1
(45) Date of Patent: *Feb. 4, 2003

(54) WEARABLE BELT INCORPORATING GAS STORAGE VESSEL COMPRISING A POLYMERIC CONTAINER SYSTEM FOR PRESSURIZED FLUIDS

(75) Inventors: John I. Izuchukwu, Wildwood, MO (US); Stan A. Sanders, Chesterfield, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/708,041

(22) Filed: Nov. 8, 2000

(51) Int. Cl.⁷ .............................................. A61M 15/00
(52) U.S. Cl. .............................. 128/202.19; 128/205.22
(58) Field of Search ................... 128/202.11, 202.18, 128/202.19, 205.13, 205.22; 285/138, 196, 216, 238, 239, 245, 256; 137/68.19, 68.23, 71

(56) References Cited

U.S. PATENT DOCUMENTS

| | | |
|---|---|---|
| 601,591 A | 3/1898 | Sherman |
| 724,129 A | 3/1903 | Schrader |
| 771,801 A | 10/1904 | Andrew |
| 1,288,857 A | 12/1918 | Farr |
| 1,348,708 A | 8/1920 | Garland |
| 1,410,405 A | 3/1922 | Johnson |
| 1,588,606 A | 6/1926 | Oden |
| 1,745,785 A | 2/1930 | Deming |
| 1,778,244 A | 10/1930 | Cadden |
| 1,786,489 A | 12/1930 | Hopkins |
| 1,901,088 A | 3/1933 | Dick |
| 2,319,024 A | 5/1943 | Wehringer |
| 2,376,353 A | 5/1945 | Grant, Jr. et al. |
| 2,380,372 A | 7/1945 | Alderfer |
| 2,430,921 A | 11/1947 | Edelmann |

(List continued on next page.)

FOREIGN PATENT DOCUMENTS

| | | |
|---|---|---|
| DE | 971689 | 3/1959 |
| DE | 2644806 A1 | 4/1978 |
| FR | 1037477 | 9/1953 |
| WO | WO 97-11734 A1 | 4/1997 |

*Primary Examiner*—Aaron J. Lewis
(74) *Attorney, Agent, or Firm*—Rothwell, Figg, Ernst & Manbeck

(57) ABSTRACT

A wearable belt includes two or more pressure packs, each including a pressure vessel for storing therein a fluid under pressure for providing a portable, and ambulatory, source of the compressed fluid. The pressure vessel is formed from a plurality of hollow chamber having either en ellipsoidal or spherical shape and interconnected by a plurality of relatively narrow conduit sections disposed between consecutive ones of the chambers. The pressure vessel includes a reinforcing filament wrapped around the interconnected chambers and interconnecting conduit sections to limit radial expansion of the chambers and conduit sections when filled with a fluid under pressure. The container system further includes a fluid transfer control system attached to the pressure vessel for controlling fluid flow into and out of the pressure vessel and a gas delivery mechanism for delivering gas from the pressure vessel to a user in a breathable manner. The pressure vessel is incorporated into the belt as two or more interconnected packs. Each pack comprises a plurality of interconnected chambers encased in a relatively rigid padded foam housing. A connecting conduit between adjacent packs is disposed within a flexible joint that can be bent or twisted, and belt straps are connected to the endmost pack housings. The belt straps include mating halves of a buckle, or other connecting feature, so that the belt can be secured around the torso of a person. The flexible joint located between adjacent relatively rigid packs permits the overall belt to conform to the body of the wearer, thereby increasing comfort and reducing the bulk created by the belt.

2 Claims, 9 Drawing Sheets

U.S. PATENT DOCUMENTS

| | | | |
|---|---|---|---|
| 2,524,052 A | * 10/1950 | Grant, Jr. | 137/68.23 |
| 2,531,700 A | 11/1950 | Porter | |
| 2,540,113 A | 2/1951 | Hartley et al. | |
| 2,764,430 A | 9/1956 | Roberts | |
| 2,771,069 A | 11/1956 | Baron | |
| 2,814,291 A | 11/1957 | Holmes | |
| 2,829,671 A | 4/1958 | Ernst et al. | |
| 2,861,569 A | 11/1958 | Emerson | |
| 3,185,500 A | 5/1965 | Luther | |
| 3,338,238 A | 8/1967 | Warncke | |
| 3,432,060 A | 3/1969 | Cowley | |
| 3,491,752 A | 1/1970 | Cowley | |
| 3,729,002 A | 4/1973 | Miller | |
| 4,060,079 A | 11/1977 | Reinhold, Jr. | |
| 4,090,509 A | 5/1978 | Smith | |
| 4,181,993 A | 1/1980 | McDaniel | |
| 4,253,454 A | 3/1981 | Warncke | |
| 4,584,996 A | * 4/1986 | Blum | 128/207.18 |
| 4,612,928 A | * 9/1986 | Tiep et al. | 128/207.18 |
| 4,665,943 A | 5/1987 | Medvick et al. | |
| 4,736,969 A | 4/1988 | Fouts | |
| 4,739,913 A | 4/1988 | Moore | |
| 4,744,356 A | * 5/1988 | Greenwood | 128/207.18 |
| 4,800,923 A | 1/1989 | Bartos | |
| 4,932,403 A | 6/1990 | Scholley | |
| 4,964,404 A | 10/1990 | Stone | |
| 4,964,405 A | 10/1990 | Arnoth | |
| 4,989,599 A | * 2/1991 | Carter | 128/207.18 |
| 4,991,876 A | 2/1991 | Mulvey | |
| 5,036,845 A | 8/1991 | Scholley | |
| 5,099,836 A | * 3/1992 | Rowland et al. | 128/207.18 |
| 5,127,399 A | 7/1992 | Scholley | |
| 5,323,953 A | 6/1994 | Adderley et al. | |
| 5,370,113 A | 12/1994 | Parsons | |
| 5,400,934 A | 3/1995 | Ducros | |
| 5,435,305 A | 7/1995 | Rankin, Sr. | |
| 5,494,469 A | 2/1996 | Heath et al. | |
| 5,503,143 A | 4/1996 | Marion et al. | |
| 5,517,984 A | 5/1996 | Sanders | |
| 5,529,061 A | 6/1996 | Sanders | |
| 5,529,096 A | 6/1996 | Rowe, Jr. et al. | |
| 5,582,164 A | 12/1996 | Sanders | |
| 5,632,268 A | 5/1997 | Ellis et al. | |
| 5,830,400 A | 11/1998 | Huvey et al. | |
| 5,839,383 A | 11/1998 | Stenning et al. | |
| 5,975,081 A | 11/1999 | Hood et al. | |
| 6,003,460 A | 12/1999 | Stenning et al. | |
| 6,047,860 A | 4/2000 | Sanders | |
| 6,187,182 B1 | 2/2001 | Reynolds et al. | |
| 6,230,737 B1 | 5/2001 | Notaro et al. | |
| 6,240,951 B1 | 6/2001 | Yori | |

* cited by examiner

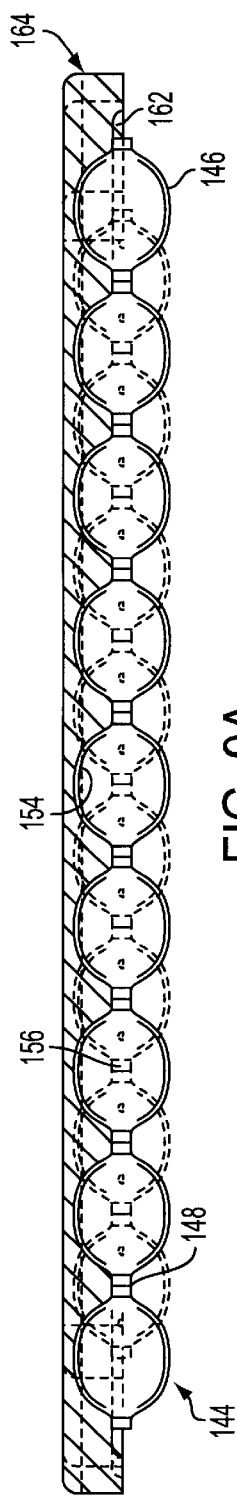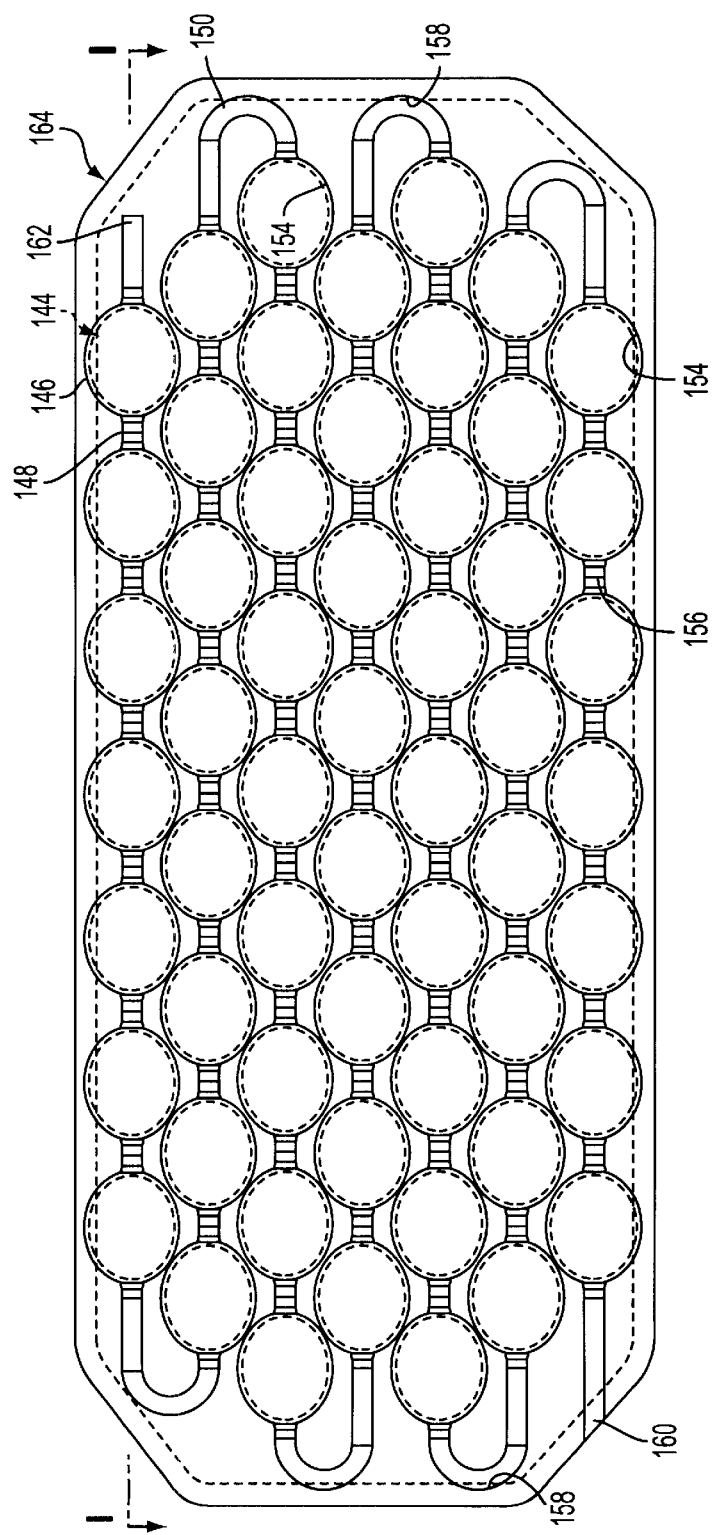

WEARABLE BELT INCORPORATING GAS STORAGE VESSEL COMPRISING A POLYMERIC CONTAINER SYSTEM FOR PRESSURIZED FLUIDS

FIELD OF THE INVENTION

The present invention is directed to belt incorporating a container system for pressurized fluids that is lightweight, flexible, and wearable around the torso of a person.

BACKGROUND OF THE INVENTION

There are many applications for a portable supply of fluid under pressure. For example, SCUBA divers and firefighters use portable, pressurized oxygen supplies incorporated into emergency breathing apparatuses. Commercial aircraft employ emergency oxygen delivery systems that are used during sudden and unexpected cabin depressurization. Military aircraft typically require supplemental oxygen supply systems as well. Such systems are supplied by portable pressurized canisters. In the medical field, gas delivery systems are provided to administer medicinal gas, such as oxygen, to a patient undergoing respiratory therapy. Supplemental oxygen delivery systems are used by patients that benefit from receiving and breathing oxygen from an oxygen supply source to supplement atmospheric oxygen breathed by the patient. For such requirements, a compact, portable supplemental oxygen delivery system is useful in a wide variety of contexts, including hospital, home care, and ambulatory settings.

High-pressure supplemental oxygen delivery systems typically include a cylinder or tank containing oxygen gas at a pressure of up to 3,000 psi. A pressure regulator is used in a high-pressure oxygen delivery system to "step down" the pressure of oxygen gas to a lower pressure (e.g., 20 to 50 psi) suitable for use in an oxygen delivery apparatus used by a person breathing the supplemental oxygen.

In supplemental oxygen delivery systems, and in other applications employing portable supplies of pressurized gas, containers used for the storage and use of compressed fluids, and particularly gases, generally take the form of cylindrical metal bottles that may be wound with reinforcing materials to withstand high fluid pressures. Such storage containers are expensive to manufacture, inherently heavy, bulky, inflexible, and prone to violent and explosive fragmentation upon rupture. Employing such containers to an emergency breathing apparatus so as to provide an ambulatory supply of oxygen can add significant undesired weight and bulk to the apparatus.

Container systems made from lightweight synthetic materials have been proposed. Scholley, in U.S. Pat. Nos. 4,932, 403; 5,036,845; and 5,127,399, describes a flexible and portable container for compressed gases which comprises a series of elongated, substantially cylindrical chambers arranged in a parallel configuration and interconnected by narrow, bent conduits and attached to the back of a vest that can be worn by a person. The container includes a liner, which may be formed of a synthetic material such as nylon, polyethylene, polypropylene, polyurethane, tetrafluoroethylene, or polyester. The liner is covered with a high-strength reinforcing fiber, such as a high-strength braid or winding of a reinforcing material such as Kevlar® aramid fiber, and a protective coating of a material, such as polyurethane, covers the reinforcing fiber.

The design described in the Scholley patents suffers a number of shortcomings which makes it impractical for use as a container for fluids stored at the pressure levels typically seen in portable fluid delivery systems such as SCUBA gear, firefighter's oxygen systems, emergency oxygen systems, and medicinal oxygen systems. The elongated, generally cylindrical shape of the separate storage chambers does not provide an effective structure for containing highly-pressurized fluids. Moreover, such large containers cannot be easily incorporated onto an emergency breathing apparatus. Also, the relatively large volume of the storage sections creates an unsafe system subject to possible violent rupture due to the kinetic energy of the relatively large volume of pressurized fluid stored in each chamber.

SUMMARY OF THE INVENTION

In accordance with aspects of the present invention, a storage system for pressurized fluids comprises a least two pressure packs for storing fluid under pressure. Each said pressure pack comprises a pressure vessel formed by a plurality of hollow chambers, each having a substantially spherical or ellipsoidal shape, a plurality of relatively narrow conduit sections, each being positioned between adjacent ones of the of hollow chambers to interconnect the hollow chambers, and a reinforcing filament wrapped around the hollow chambers and the conduit sections. Each pressure pack also includes a housing encasing the pressure vessel.

The storage system further includes a flexible fluid transfer conduit connecting the pressure vessels of adjacent pressure pack, a fluid transfer control system for controlling flow of fluid into and out of the pressure vessels, and one or more belt straps operatively attached to the pressure packs for securing around the torso of a person to provide an ambulatory supply of fluid stored in the pressure vessels.

Other objects, features, and characteristics of the present invention will become apparent upon consideration of the following description and the appended claims with reference to the accompanying drawings, all of which form a part of the specification, and wherein like reference numerals designate corresponding parts in the various figures.

DESCRIPTION OF THE DRAWINGS

FIG. 9 is a plan view of a container system according to the present invention secured within a conforming shell of a housing for a portable pressurized fluid pack.

FIG. 9A is a transverse section along the line I—I in FIG. 9.

DETAILED DESCRIPTION OF THE INVENTION

With reference to the figures, exemplary embodiments of the invention will now be described. These embodiments illustrate principles of the invention and should not be construed as limiting the scope of the invention.

Figure 1:
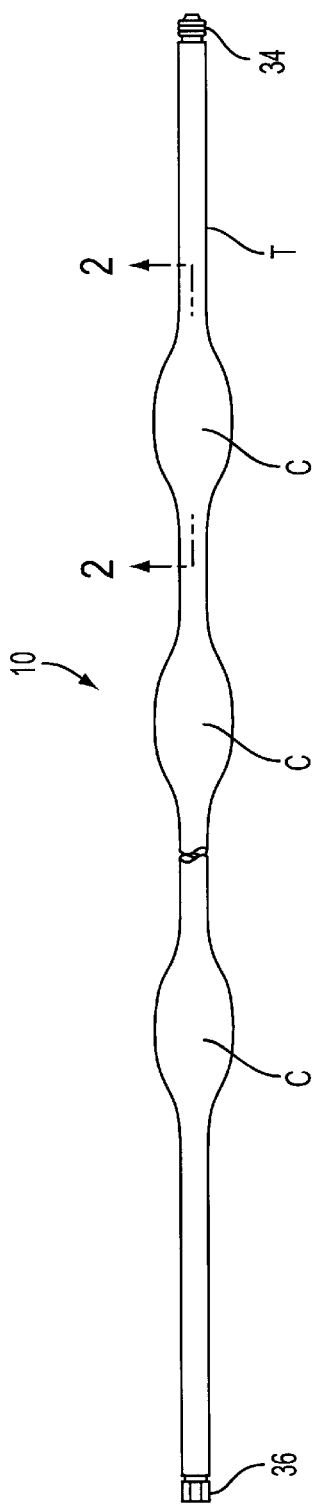
FIG. 1 is a broken side elevational view of a plurality of aligned, rigid, generally ellipsoidal chambers interconnected by a tubular core.
Figure 2A:
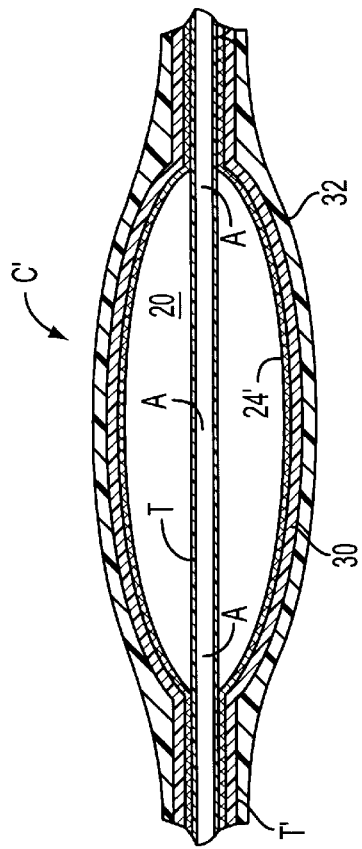
FIG. 2A is an enlarged horizontal sectional view taken along the line 2—2 in FIG. 1 showing an alternate embodiment.
Figure 2:
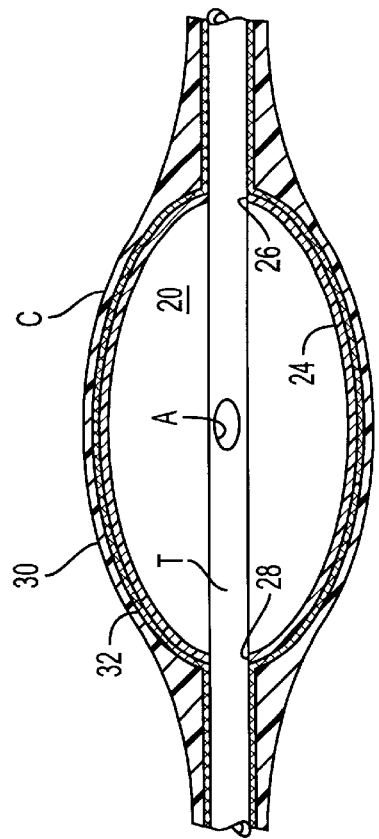
FIG. 2 is an enlarged horizontal sectional view taken along the line 2—2 in FIG. 1.

As shown in FIGS. 1 and 2, U.S. Pat. No. 6,047,860 (the disclosure of which is hereby incorporated by reference) to Sanders, an inventor of the present invention, discloses a container system 10 for pressurized fluids including a plurality of form-retaining, generally ellipsoidal chambers C interconnected by a tubular core T. The tubular core extends through each of the plurality of chambers and is sealingly secured to each chamber. A plurality of longitudinally-spaced apertures A are formed along the length of the tubular core, one such aperture being disposed in the interior space 20 of each of the interconnected chambers so as to permit infusion of fluid to the interior space 20 during filling and effusion of the fluid from the interior space 20 during fluid delivery or transfer to another container. The apertures are sized so as to control the rate of evacuation of pressurized fluid from the chambers. Accordingly, a low fluid evacuation rate can be achieved so as to avoid a large and potentially dangerous burst of kinetic energy should one or more of the chambers be punctured (i.e., penetrated by an outside force) or rupture.

The size of the apertures A will depend upon various parameters, such as the volume and viscosity of fluid being contained, the anticipated pressure range, and the desired flow rate. In general, smaller diameters will be selected for gasses as opposed to liquids. Thus, the aperture size may generally vary from about 0.010 to 0.125 inches. Although only a single aperture A is shown in FIG. 2, more than one aperture A can be formed in the tube T within the interior space 20 of the shell 24. In addition, each aperture A can be formed in only one side of the tube T, or the aperture A may extend through the tube T.

Referring to FIG. 2, each chamber C includes a generally ellipsoidal shell 24 molded of a suitable synthetic plastic material and having open front and rear ends 26 and 28. The diameters of the holes 26 and 28 are dimensioned so as to snugly receive the outside diameter of the tubular core T. The tubular core T is attached to the shells 24 so as to form a fluid tight seal therebetween. The tubular core T is preferably bonded to the shells 24 by means of light, thermal, or ultrasonic energy, including techniques such as, ultrasonic welding, radio frequency energy, vulcanization, or other thermal processes capable of achieving seamless circumferential welding. The shells 24 may be bonded to the tubular core T by suitable ultraviolet light-curable adhesives, such as 3311 and 3341 Light Cure Acrylic Adhesives available from Loctite Corporation, having authorized distributors throughout the world. The exterior of the shells 24 and the increments of tubular core T between such shells are wrapped with suitable reinforcing filaments 30 to increase the hoop strength of the chambers C and tubular core T and thereby resist bursting of the shells and tubular core. A protective synthetic plastic coating 32 is applied to the exterior of the filament wrapped shells and tubular core T.

More particularly, the shells 24 may be either roto molded, blow molded, or injection molded of a synthetic plastic material such as TEFLON or fluorinated ethylene propylene. Preferably, the tubular core T will be formed of the same material. The reinforcing filaments 30 may be made of a carbon fiber, Kevlar® or Nylon. The protective coating 32 may be made of urethane to protect the chambers and tubular core against abrasions, UV rays, moisture, or thermal elements. The assembly of a plurality of generally ellipsoidal chambers C and their supporting tubular core T can be made in continuous strands of desired length. In the context of the present disclosure, unless stated otherwise, the term "strand" will refer to a discrete length of interconnected chambers.

As shown in FIG. 2A, the tube T can be co-formed, such as by co-extrusion, along with shells 24' and tubular portions T' integrally formed with the shells 24' and which directly overlie the tube T between adjacent shells 24'. Furthermore, as also shown in FIG. 2A, more than one aperture A may be formed in the tube T within the interior 20 of the shell 24'. The co-formed assembly comprised of the shells 24', tubular portions T', and tube T can be wrapped with a layer of reinforcing filaments 30 and covered with a protective coating 32 as described above.

The inlet or front end of the tubular core T may be provided with a suitable threaded male fitting 34. The discharge or rear end of a tubular core T may be provided with a threaded female fitting 36. Such male and female fittings provide a pressure-type connection between contiguous strands of assemblies of chambers C interconnected by tubular cores T and provide a mechanism by which other components, such as gauges and valves, can be attached to the interconnected chambers. A preferred structure for attaching such fittings is described below.

Figure 3:
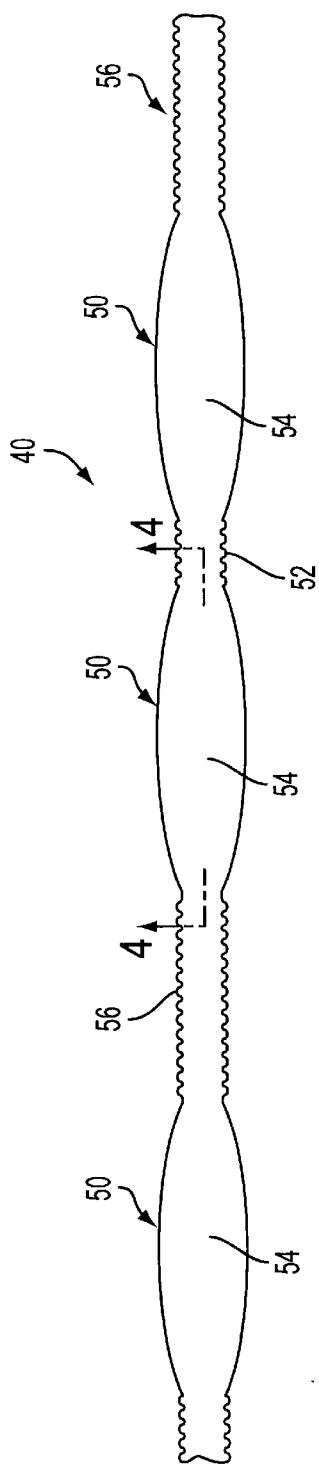
FIG. 3 is a side elevational view of a portion of a container system of the present invention.

A portion of a pressure vessel constructed in accordance with principles of the present invention is designated generally by reference number 40 in FIG. 3. The pressure vessel 40 includes a plurality of fluid storage chambers 50 having a preferred ellipsoidal shape and having hollow interiors 54. The individual chambers 50 are pneumatically interconnected with each other by connecting conduit sections 52 and 56 disposed between adjacent ones of the chambers 50. Conduit sections 56 are generally longer than the conduit sections 52. The purpose of the differing lengths of the conduit sections 52 and 56 will be described in more detail below.

Figure 4:
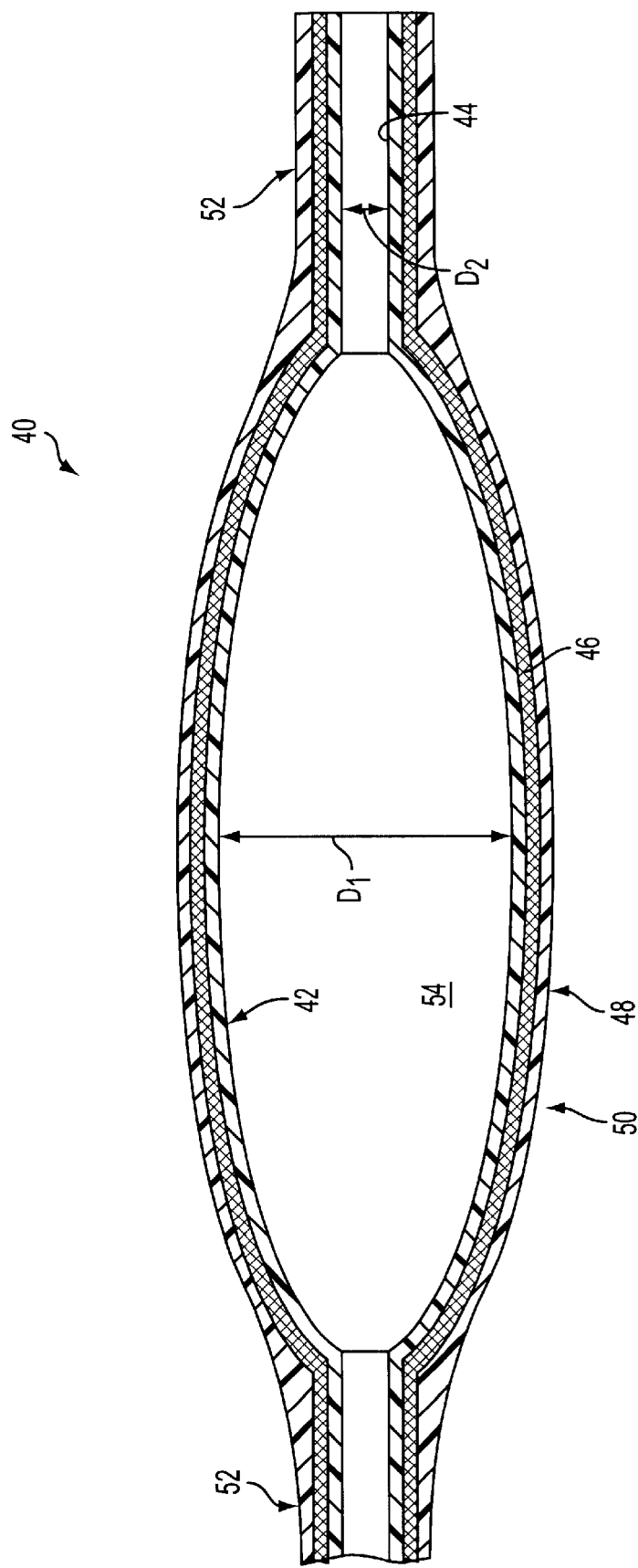
FIG. 4 is a partial longitudinal sectional view along line 4—4 in FIG. 3.

FIG. 4 shows an enlarged longitudinal section of a single hollow chamber 50 and portions of adjacent conduit sections 52 of the pressure vessel 40. The pressure vessel 40 preferably has a layered construction including polymeric hollow shells 42 with polymeric connecting conduits 44 extended from opposed open ends of the shells 42. The pressure vessel 40 includes no tubular core, such as tubular core T shown in FIGS. 2 and 2A, extending through the hollow shells 42.

The polymeric shells 42 and the polymeric connecting conduits 44 are preferably formed from a synthetic plastic material such as Teflon or fluorinated ethylene propylene and may be formed by any of a number of known plastic-forming techniques such as extrusion, roto molding, chain blow molding, or injection molding.

Materials used for forming the shells 42 and connecting conduits 44 are preferably moldable and exhibit high tensile strength and tear resistance. Most preferably, the polymeric hollow shells 42 and the polymeric connecting conduits 44 are formed from a thermoplastic polyurethane elastomer manufactured by Dow Plastics under the name Pellethane® 2363-90AE, a thermoplastic polyurethane elastomer manufactured by the Bayer Corporation, Plastics Division under the name Texin® 5286, a flexible polyester manufactured by Dupont under the name Hytrel®, or polyvinyl chloride from Teknor Apex.

In a preferred configuration, the volume of the hollow interior 54 of each chamber 50 is within a range of capacities configurable for different applications, with a most preferred volume of about thirty (30) milliliters. It is not necessary that each chamber have the same dimensions or have the same capacity. It has been determined that a pressure vessel 40 having a construction as will be described below will undergo a volume expansion of 7–10% when subjected to an internal pressure of 2000 psi. In a preferred configuration, the polymeric shells 42 each have a longitudinal length of about 3.0–3.5 inches, with a most preferred length of 3.250–3.330 inches, and a maximum outside diameter of about 0.800 to 1.200 inches, with a most preferred diameter of 0.0951–1.050 inches. The conduits 44 have an inside diameter $D_2$ preferably ranging from 0.1250–0.300 inches with a most preferred range of about 0.175–0.250 inches. The hollow shells 42 have a typical wall thickness ranging from 0.03 to 0.05 inches with a most preferred typical thickness of about 0.04 inches. The connecting conduits 44 have a wall thickness ranging from 0.03 to 0.10 inches and preferably have a typical wall thickness of about 0.040 inches, but, due to the differing amounts of expansion experienced in the hollow shells 42 and the conduits 44 during a blow molding forming process, the conduits 44 may actually have a typical wall thickness of about 0.088 inches.

The exterior surface of the polymeric hollow shells 42 and the polymeric connecting conduits 44 is preferably wrapped with a suitable reinforcing filament fiber 46. Filament layer 46 may be either a winding or a braid (preferably a triaxial braid pattern having a nominal braid angle of 75 degrees) and is preferably a high-strength aramid fiber material such as Kevlar® (preferably 1420 denier fibers), carbon fibers, or nylon, with Kevlar® being most preferred. Other potentially suitable filament fiber material may include thin metal wire, glass, polyester, or graphite. The Kevlar winding layer has a preferred thickness of about 0.035 to 0.055 inches, with a thickness of about 0.045 inches being most preferred.

A protective coating 48 may be applied over the layer of filament fiber 46. The protective coating 48 protects the shells 42, conduits 44, and the filament fiber 46 from abrasions, UV rays, thermal elements, or moisture. Protective coating 32 is preferably a sprayed-on synthetic plastic coating. Suitable materials include polyvinyl chloride and polyurethane. The protective coating 32 may be applied to the entire pressure vessel 40, or only to more vulnerable portions thereof. Alternatively, the protective coating 32 could be dispensed with altogether if the pressure vessel 40 is encased in a protective, moisture-impervious housing.

The inside diameter $D_1$ of the hollow shell 42 is preferably much greater than the inside diameter $D_2$ of the conduit section 44, thereby defining a relatively discrete storage chamber within the hollow interior 54 of each polymeric shell 42. This serves as a mechanism for reducing the kinetic energy released upon the rupturing of one of the chambers 50 of the pressure vessel 40. That is, if one of the chambers 50 should rupture, the volume of pressurized fluid within that particular chamber would escape immediately. Pressurized fluid in the remaining chambers would also move toward the rupture, but the kinetic energy of the escape of the fluid in the remaining chambers would be regulated by the relatively narrow conduit sections 44 through which the fluid must flow on its way to the ruptured chamber. Accordingly, immediate release of the entire content of the pressure vessel is avoided.

Figure 5:
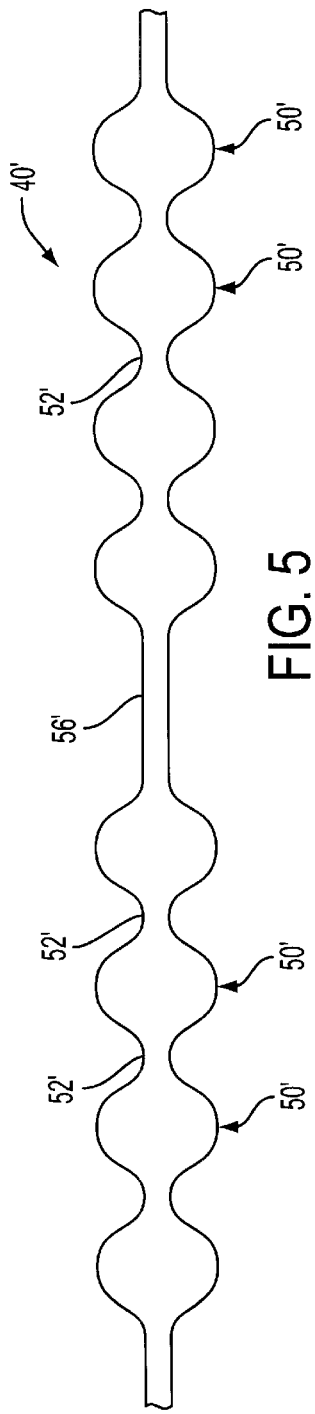
FIG. 5 is a side elevational view of an alternative embodiment of the container system of the present invention.
Figure 5A:
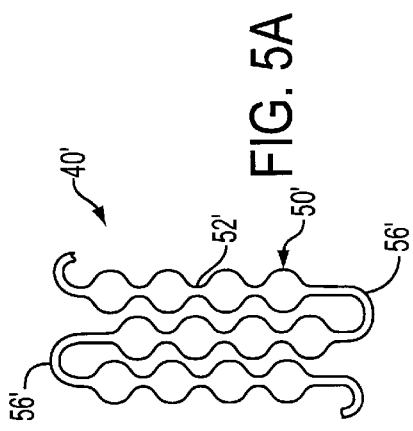
FIG. 5A is a partial view of the container system of FIG. 5 arranged in a sinuous configuration.

An alternate pressure vessel 40' is shown in FIGS. 5 and 5A. Pressure vessel 40' includes a plurality of hollow chambers 50' having a generally spherical shape connected by conduit sections 52' and 56'. As shown in FIG. 5A, one particular configuration of the pressure vessel 40' is to bend it back-and-forth upon itself in a sinuous fashion. The pressure vessel 40' is bent at the elongated conduit sections 56', which are elongated relative to the conduit sections 52' so that they can be bent without kinking or without adjacent hollow chambers 50' interfering with each other. Accordingly, the length of the conduit sections 56' can be defined so as to permit the pressure vessel to be bent thereat without kinking and without adjacent hollow chambers 50' interfering with each other. In general, a connecting conduit section 56' of sufficient length can be provided by omitting a chamber 50' in the interconnected series of chambers 50'. The length of a long conduit section 56', however, need not necessarily be as long as the length of a single chamber 50'.

Both ellipsoidal and the spherical chambers are preferred, because such shapes are better suited than other shapes, such as cylinders, to withstand high internal pressures. Spherical chambers 50' are not, however, as preferable as the generally ellipsoidal chambers 50 of FIGS. 3 and 4, because, the more rounded a surface is, the more difficult it is to apply a consistent winding of reinforcing filament fiber. Filament fibers, being applied with axial tension, are more prone to slipping on highly rounded, convex surfaces.

A portable pressure pack 60 employing a pressure vessel 40 as described above is shown in FIG. 6. Note that the pressure pack 60 includes a pressure vessel 40 having generally ellipsoidal hollow chambers 50. It should be understood, however, that a pressure vessel 40 of a type having generally spherical hollow chambers as shown in FIGS. 5 and 5A could be employed in the pressure pack 60 as well. The pressure vessel 40 is arranged as a continuous, serial strand 58 of interconnected chambers 50 bent back-and-forth upon itself in a sinuous fashion with all of the chambers lying generally in a common plane. In general, the axial arrangement of any strand of interconnected chambers can be an orientation in any angle in X-Y-Z Cartesian space. Note again, in FIG. 6, that elongated conduit sections 56 are provided. Sections 56 are substantially longer than conduit sections 52 and are provided to permit the pressure vessel 40 to be bent back upon itself without kinking the conduit section 56 or without adjacent chambers 50 interfering with one another. Again, an interconnecting conduit 56 of sufficient length for bending can be provided by omitting a chamber 50 from the strand 58 of interconnected chambers.

The pressure vessel 40 is encased in a protective housing 62. Housing 62 may have a handle, such as an opening 64, provided therein.

A fluid transfer control system 76 is pneumatically connected to the pressure vessel 40 and is operable to control transfer of fluid under pressure into or out of the pressure vessel 40. In the embodiment illustrated in FIG. 6, the fluid transfer control system includes a one-way inlet valve 70 (also known as a fill valve) pneumatically connected (e.g., by a crimp or swage) to a first end 72 of the strand 58 and a one-way outlet valve/regulator 66 pneumatically connected (e.g., by a crimp or swage) to a second end 74 of the pressure vessel 40. In general, the inlet valve 70 includes a mechanism permitting fluid to be transferred from a pressurized fluid fill source into the pressure vessel 40 through inlet valve 70 and to prevent fluid within the pressure vessel 40 from escaping through the inlet valve 70. Any suitable one-way inlet valve, well known to those of ordinary skill in the art, may be used.

The outlet valve/regulator 66 generally includes a well known mechanism permitting the outlet valve/regulator to be selectively configured to either prevent fluid within the pressure vessel 40 from escaping the vessel through the valve 66 or to permit fluid within the pressure vessel 40 to escape the vessel in a controlled manner through the valve 66. Preferably, the outlet valve/regulator 66 is operable to "step down" the pressure of fluid exiting the pressure vessel 40. For example, in typical medicinal applications of ambulatory oxygen, oxygen may be stored within the tank at up to 3,000 psi, and a regulator is provided to step down the outlet pressure to 20 to 50 psi. The outlet valve/regulator 66 may include a manually-operable control knob 68 for permitting manual control of a flow rate therefrom. Any suitable regulator valve, well known to those of ordinary skill in the art, may be used.

A pressure relief valve (not shown) is preferably provided to accommodate internal pressure fluctuations due to thermal cycling or other causes.

Figure 6:
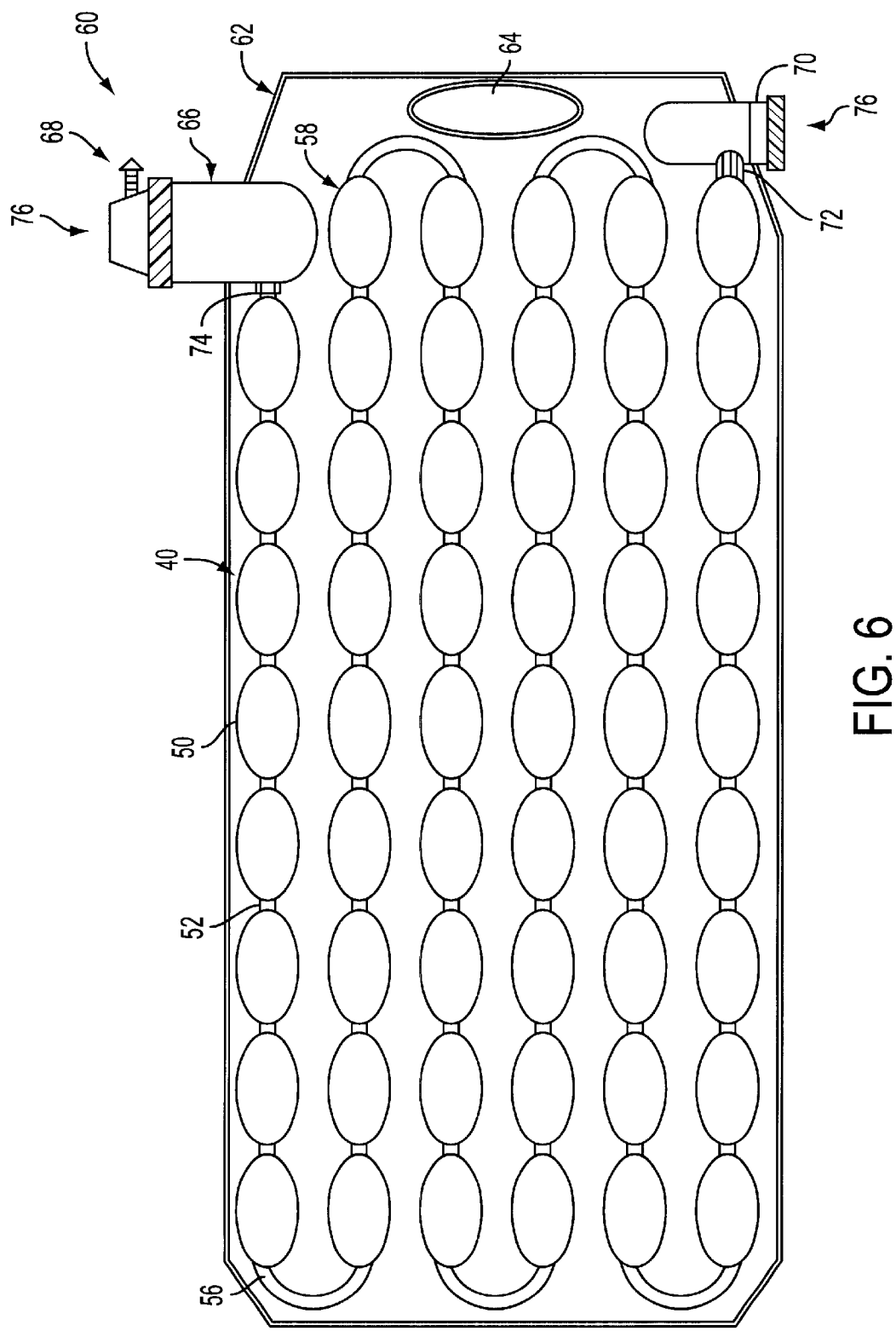
FIG. 6 is a portable pressurized fluid pack employing a container system according to the present invention.

In FIG. 6, the pressure vessel 40, inlet valve 70, and the outlet valve/regulator 66 are shown exposed on top of the housing 62. Preferably, the housing comprises dual halves of, for example, preformed foam shells as will be described in more detail below. For the purposes of illustrating the structure of the embodiment of FIG. 6, however, a top half of the housing 62 is not shown. It should be understood, however, that a housing would substantially encase the pressure vessel 40 and at least portions of the outlet valve/regulator 66 and the inlet valve 70.

Figure 7:
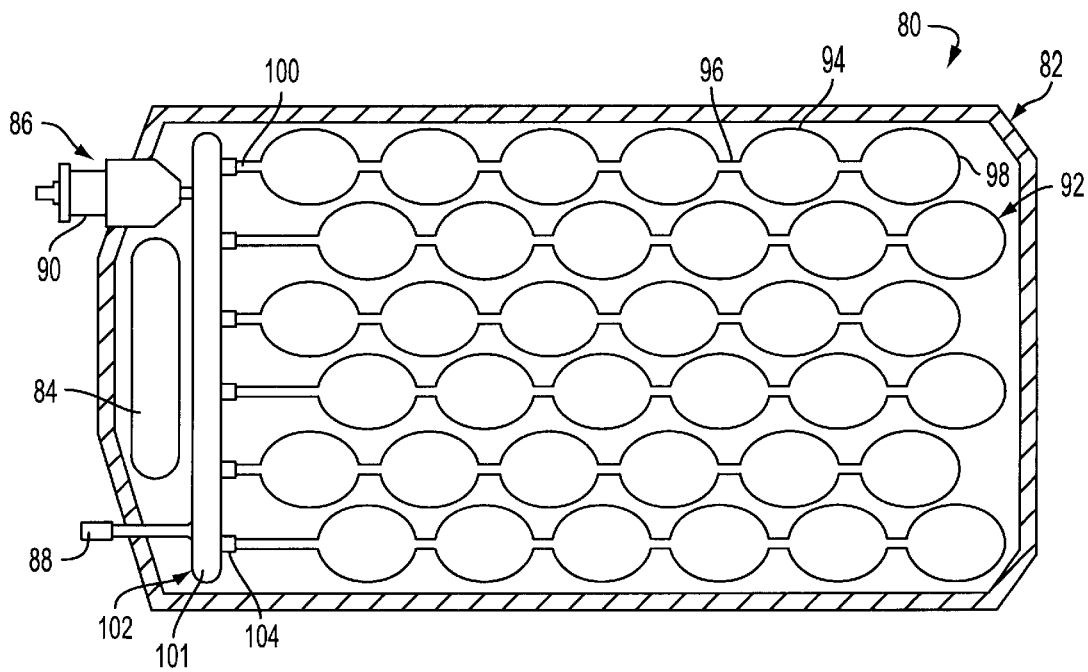
FIG. 7 is an alternate embodiment of a pressurized fluid pack employing the container system of the present invention.

FIG. 7 shows an alternate embodiment of a portable pressure pack generally designated by reference number 80. The pressure pack 80 includes a pressure vessel formed by a number of strands 92 of individual chambers 94 serially interconnected by interconnecting conduit sections 96 and arrange generally in parallel to each other. In the embodiment illustrated in FIG. 7, the pressure vessel includes six individual strands 92, but the pressure pack may include fewer than or more than six strands.

Each of the strands 92 has a first closed end 98 at the endmost of the chambers 94 of the strand 92 and an open terminal end 100 attached to a coupling structure defining an inner plenum, which, in the illustrated embodiment, comprises a distributor 102. The distributor 102 includes an elongated, generally hollow body 101 defining the inner plenum therein. Each of the strands 92 of interconnected chambers is pneumatically connected at its respective terminal end 100 by a connecting nipple 104 extending from the elongated body 101, so that each strand 92 of interconnected chambers 94 is in pneumatic communication with the inner plenum inside the distributor 102. Each strand 92 may be connected to the distributor 102 by a threaded interconnection, a crimp, or a swage, or any other suitable means for connecting a high pressure polymeric tube to a rigid fitting. A fluid transfer control system 86 is pneumatically connected to the distributor 102. In the illustrated embodiment, the fluid transfer control system 86 includes a one-way inlet valve 88 and a one-way outlet/regulator 90 pneumatically connected at generally opposite ends of the body 101 of the distributor 102.

The strands 92 of interconnected chambers 94, the distributor 102, and at least portions of the inlet valve 88 and the outlet valve/regulator 90 are encased within a housing 82, which may include a handle 84, as illustrated in FIG. 7, to facilitate carrying of the pressure pack 80.

Figure 8:
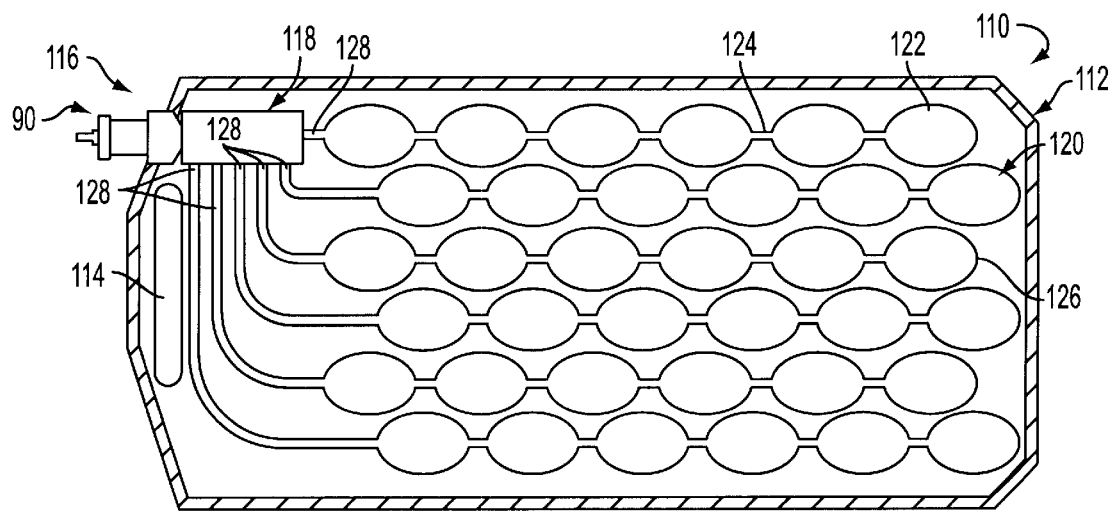
FIG. 8 is still another alternate embodiment of a pressurized fluid pack employing a container system according to the present invention.

In FIG. 8 is shown still another alternative embodiment of a pressure pack generally designated by reference number 110. The pressure pack 110 includes a pressure vessel comprised of a number of generally parallel strands 120 of hollow chambers 122 serially interconnected by interconnecting conduit sections 124. Each of the strands 120 has a closed end 126 at the endmost of its chambers 122 and an open terminal end 128 attached to a coupling structure defining an inner plenum. In the illustrated embodiment, the coupling structure comprises a manifold 118 to which is pneumatically attached each of the respective terminal ends 128 of the strands 120. Each strand 120 may be connected to the manifold 118 by a threaded interconnection, a crimp, or a swage, or any other suitable means for connecting a high pressure polymeric tube to a rigid fitting. A fluid transfer control system 116 is attached to the manifold 118, and, in the illustrated embodiment, comprises a outlet valve/regulator 90 and an inlet valve (not shown).

The hollow chambers of the pressure vessels described above and shown in FIGS. 5A, 6, 7, and 8 can be of the type shown in FIGS. 2 and 2A having an internal perforated tubular core, or they can be of the type shown in FIG. 4 having no internal tubular core.

FIGS. 9 and 9A show one-half of a foam shell, generally indicated at 164, for encasing a pressure vessel 144 to form a housing for a portable pressure pack. The pressure vessel 144 shown in FIG. 9 includes a sinuous arrangement of generally spherical chambers 146 serially interconnected by short interconnecting conduit sections 148 and longer, bendable interconnecting conduit sections 150. The foam shell 164 is preferably a molded synthetic foam "egg crate" design. That is, the shell 164 includes a plurality of chamber recesses 154 serially interconnected by short, straight interconnecting channels 156 and long, curved interconnecting channels 158. The chamber recesses 154 and the interconnecting channels 156 and 158 are arranged in the preferred arrangement of the chambers 146 and interconnecting conduits 148 and 150 of the pressure vessel 144. Alternatively, the chamber recesses 154 and interconnecting channels 156, 158 could be configured in other preferred arrangements such as, for example, those arrangements shown in FIGS. 6, 7, and 8.

The foam shell 164 may be formed from neoprene padding or a polyurethane-based foam. Most preferably, the foam shell is formed from a closed cell, skinned foam having a liquid impervious protective skin layer. Suitable materials include polyethylene, polyvinyl chloride, and polyurethane. The use of a self-skinning, liquid impervious foam may eliminate the need for the protective synthetic plastic coating 48 (see FIG. 4) applied directly onto the reinforcing filament layer. A fire retardant additive, such as, for example, fire retardant additives available from Dow Chemical, can be added to the foam material of the foam shells.

A second foam shell (not shown) has chamber recesses and interconnecting channels arranged in a configuration that registers with the chamber recesses 154 and the interconnecting channels 156 and 158 of the foam shell 164. The two foam shells are arranged in mutually-facing relation and closed upon one another to encase the pressure vessel 144. The mating foam shells are thereafter adhesively-attached to one another at marginal edge portions thereof.

Suitable adhesives for attaching the mating foam shell halves include pressure sensitive adhesives.

Figure 10:
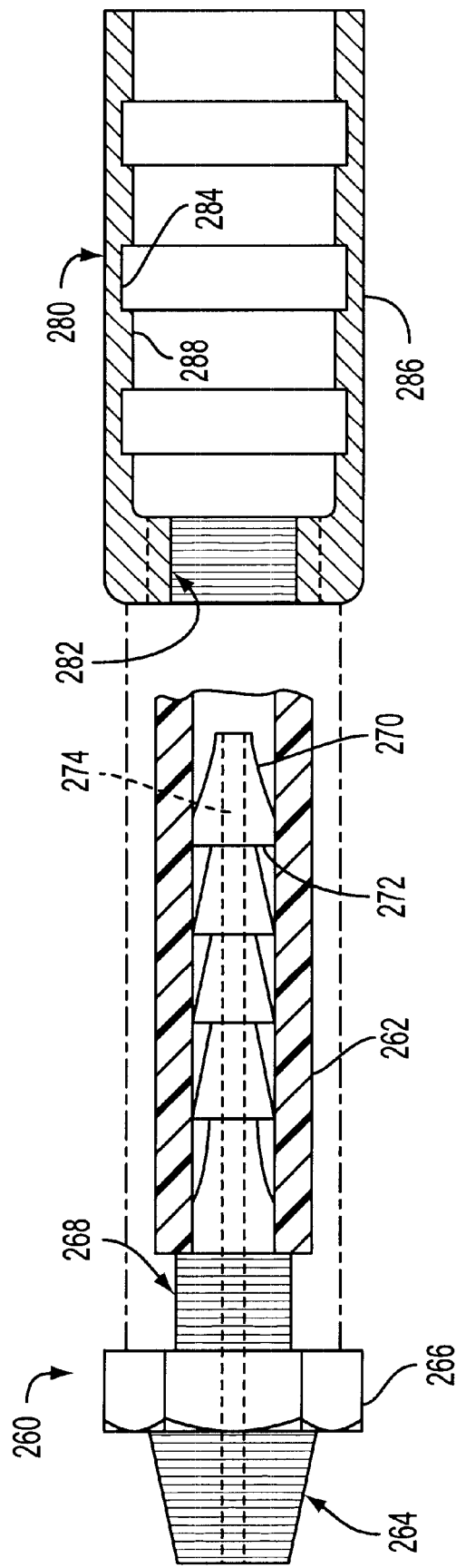
FIG. 10 is a partial, exploded view in longitudinal section of a system for securing a polymeric tube to a mechanical fitting.

FIG. 10 shows a preferred arrangement for attaching a mechanical fitting 260 to a polymeric tube 262 in a manner that can withstand high pressures within the tube 262. Such fittings 260 can be attached to the ends of a continuous strand of serially connected hollow chambers for connecting inlet and outlet valves at the opposite ends. For example, fittings 34 and 36 shown in FIG. 1 could be attached in the manner to be described. The mechanical fitting 260 has a body portion, which, in the illustrated embodiment includes a threaded end 264 to which can be attached another component, such as a valve or a gauge, and a faceted portion 266 that can be engaged by a tool such as a wrench. The body portion is preferably made of brass. End 264 is shown as an exteriorly threaded male connector portion, but could be an interiorly threaded female connector portion. An exteriorly threaded collar 268 extends to the right of the faceted portion 266. An inserting projection 270 extends from the threaded collar 268 and has formed thereon a series of barbs 272 of the "Christmas tree" or corrugated type that, due to the angle of each of the barbs 272, permits the projection 270 to be inserted into the polymeric tube 262, as shown, but resists removal of the projection 270 from the polymeric tube 262. A channel 274 extends through the entire mechanical fitting 260 to permit fluid transfer communication through the fitting 260 into a pressure vessel.

A connecting ferrule 280 has a generally hollow, cylindrical shape and has an interiorly threaded opening 282 formed at one end thereof. The remainder of the ferrule extending to the right of the threaded opening 282 is a crimping portion 286. The ferrule 280 is preferably made of 6061 T6 aluminum. The crimping portion 286 has internally-formed ridges 288 and grooves 284. The inside diameter of the ridges 288 in an uncrimped ferrule 280 is preferably greater than the outside diameter of the polymeric tube 262 to permit the uncrimped ferrule to be installed over the tube.

Attachment of the fitting 260 to the tube 262 is affected by first screwing the threaded collar 268 into the threaded opening 282 of the ferrule 280. Alternatively, the ferrule 280 can be connected to the fitting 260 by other means. For example, the ferrule 280 may be secured to the fitting 260 by a twist and lock arrangement or by welding (or soldering or brazing) the ferrule 280 to the fitting 260. The polymeric tube 262 is then inserted over the inserting projection 270 and into a space between the crimping portion 286 and the inserting projection 270. The crimping portion 286 is then crimped, or swaged, radially inwardly in a known manner to thereby urge the barbs 272 and the ridges 288 and grooves 284 into locking deforming engagement with the tube 262. Accordingly, the tube 262 is securely held to the fitting 260 by both the frictional engagement of the tube 262 with the barbs 272 of the inserting projection 270 as well as the frictional engagement of the tube 262 with the grooves 284 and ridges 288 of the ferrule 280, which itself is secured to the fitting 260, e.g., by threaded engagement of threaded collar 268 with threaded opening 282.

A connecting arrangement of the type shown in FIG. 10 could also be used, for example, for attaching the strands 92 of interconnected chambers to the connecting nipples 104 of the distributor 102 in FIG. 7 or to attach the strands of interconnected chambers 120 to the connecting nipples 138 and 140 of the manifold 118 of FIG. 8.

Figure 11:
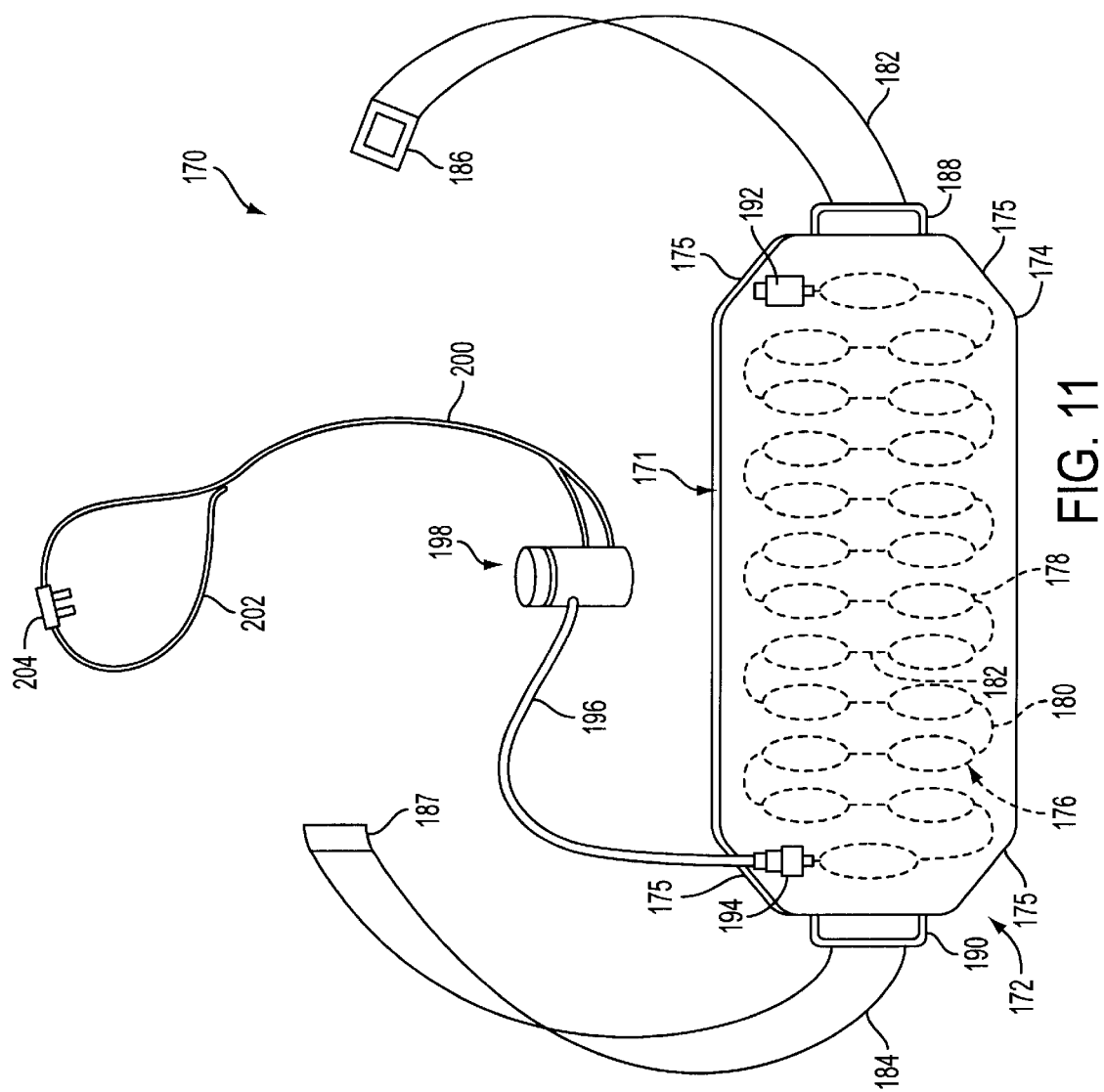
FIG. 11 is a perspective view of a wearable, portable oxygen delivery system incorporating a container system according to the present invention.

A configuration of a portable pressure pack incorporated into a wearable carrier garment is shown in FIG. 11. A wearable gas supply system 170 includes a pressure vessel 176 carried in a garment that takes the form of a cummerbund-style belt. The belt 172 includes the pressure vessel 176 having a plurality of chambers 178 serially interconnected by short straight conduit sections 182 and long bent conduit sections 180. The pressure vessel 176 can be of the type shown in FIGS. 2 and 2A, having an internal perforated tubular core, or they can be of the type shown in FIG. 4 having no internal tubular core. The chambers 178 are of a polymeric, filament winding-reinforced construction, as described above, and are preferably ellipsoidal, but may be spherical.

The pressure vessel 176 is encased in a padded housing 174 formed of a suitable padding material, such as neoprene. The housing 174 may comprise anterior and posterior cushioning layers secured to one another with a suitable adhesive with the pressure vessel and flow control system sandwiched in between. The anterior and posterior pads may each be of the egg crate-type design shown in FIGS. 9 and 9A and described above, including recesses, or cavities, each conforming to one half of the chambers of the pressure vessel 176. A liquid impervious layer is preferably applied to the outer surface of the housing 174. Padded housing 174 preferably has angled corners 175 to facilitate the comfort for the wearer by avoiding possible sharp jabs that might be inflicted by a more pointed corner. In a preferred arrangement, the chambers 178 of the pressure vessel 176 are elongated ellipsoidal chambers and are arranged in a generally vertical, mutually parallel arrangement as shown by hidden lines.

Belt straps 182 and 184 may be attached to the padded housing 174 by any suitable means, such as by means of attaching brackets 188 and 190, respectively. Belt straps 182, 184 may comprise nylon web straps and preferably have adjustable lengths. Attaching brackets 188, 190 may be adhesively secured between the opposed layers of padding forming the padded housing 174. Alternatively, straps 182 and 184 could be provided as one continuous strap extending completely across the padded housing 174, and attaching brackets 188 190 can be omitted. Such a design has certain advantages in that it eliminates tensile forces at the attaching brackets 188 and 190 that can separate the brackets from the housing 174. Strap 182 can include a buckle 186 of conventional design that attaches to an end 187 of the other strap 184.

A one-way inlet valve 192 is connected to one end of the pressure vessel 176, and a one-way outlet valve/regulator 194 is connected to the opposite end of the pressure vessel 176. Both the inlet valve 192 and the outlet valve 194 are vertically oriented and are disposed on an outer face of the housing 174 and positioned so that the respective tops thereof do not project above a top edge 171 of the housing 174 and most preferably do not project above the adjacent angled corners 175. By having the inlet valve 192 and the outlet valve 194 oriented vertically and positioned on the front face of the housing 174 and recessed below a top edge thereof, there is less likelihood that the person wearing the belt 172 will experience discomfort from being jabbed by either of the valves 192 or 194.

A gas delivery mechanism is pneumatically connected to the fluid transfer control system for delivering metered fluid from the pressure vessel to a person. In the illustrated embodiment, an oxygen delivery system is connected to the outlet valve 194. More particularly, in the illustrated embodiment, a flexible tube 196 connects the outlet valve/regulator 194 to a flow control valve 198. Flow control valve 198 is preferably a pneumatic demand oxygen conservor valve or an electronic oxygen conservor valve. Pneumatic demand oxygen conservor valves are constructed and arranged to dispense a pre-defined volume of low pressure oxygen (referred to as a "bolus" of oxygen) to a patient in response to inhalation by the patient and to otherwise suspend oxygen flow from the pressure vessel during non-inhaling episodes of the patient's breathing cycle. Pneumatic demand oxygen conservor valves are described in U.S. Pat. No. 5,360,000 and in PCT Publication No. WO 97/11734A1, the respective disclosures of which are hereby incorporated by reference. A most preferred pneumatic demand oxygen conservor of the type that can be clipped onto the belt of a person receiving the supplemental oxygen is disclosed in U.S. patent application Ser. No. 09/435,174 filed Nov. 5, 1999, the disclosure of which is hereby incorporated by reference.

A dual lumen flexible tube 200 extends from the flow control valve 198 toward a loop 202 formed by the two lumen of the tube 200, the respective ends of which connect to a gas delivery mechanism, such as a dual lumen nasal cannula 204. A dual lumen nasal cannula communicates the patient's breathing status through one of the lumen of the dual lumen tube 200 to the flow control valve 198 and delivers oxygen to the patient during inhalation through the other lumen of the dual lumen tube 200. A suitable dual lumen nasal cannula is described in U.S. Pat. No. 4,989,599, the disclosure of which is hereby incorporated by reference.

A breathing mask may be employed instead of a nasal cannula.

Accordingly, it can be appreciated that the cummerbund-style belt 172 shown in FIG. 11 can provide a lightweight, unobtrusive, portable supply of pressurized fluid, such as oxygen, and can be worn around the lower torso of the person receiving the fluid with the padded housing 174 in front of the user against his or her abdomen or behind the user against his or her lower back.

In the embodiment illustrated in FIG. 11, the pressure vessel 176 comprises a single continuous strand of interconnected chambers 178 arranged in a sinuous configuration. Alternatively, however, the pressure vessel of the cummerbund-style belt shown in FIG. 11 can include a number of separate strands of interconnected chambers pneumatically coupled together by a coupling structure defining an inner plenum, such as pressure vessels having a distributor or manifold as shown in FIGS. 7 and 8, respectively.

Figure 12:
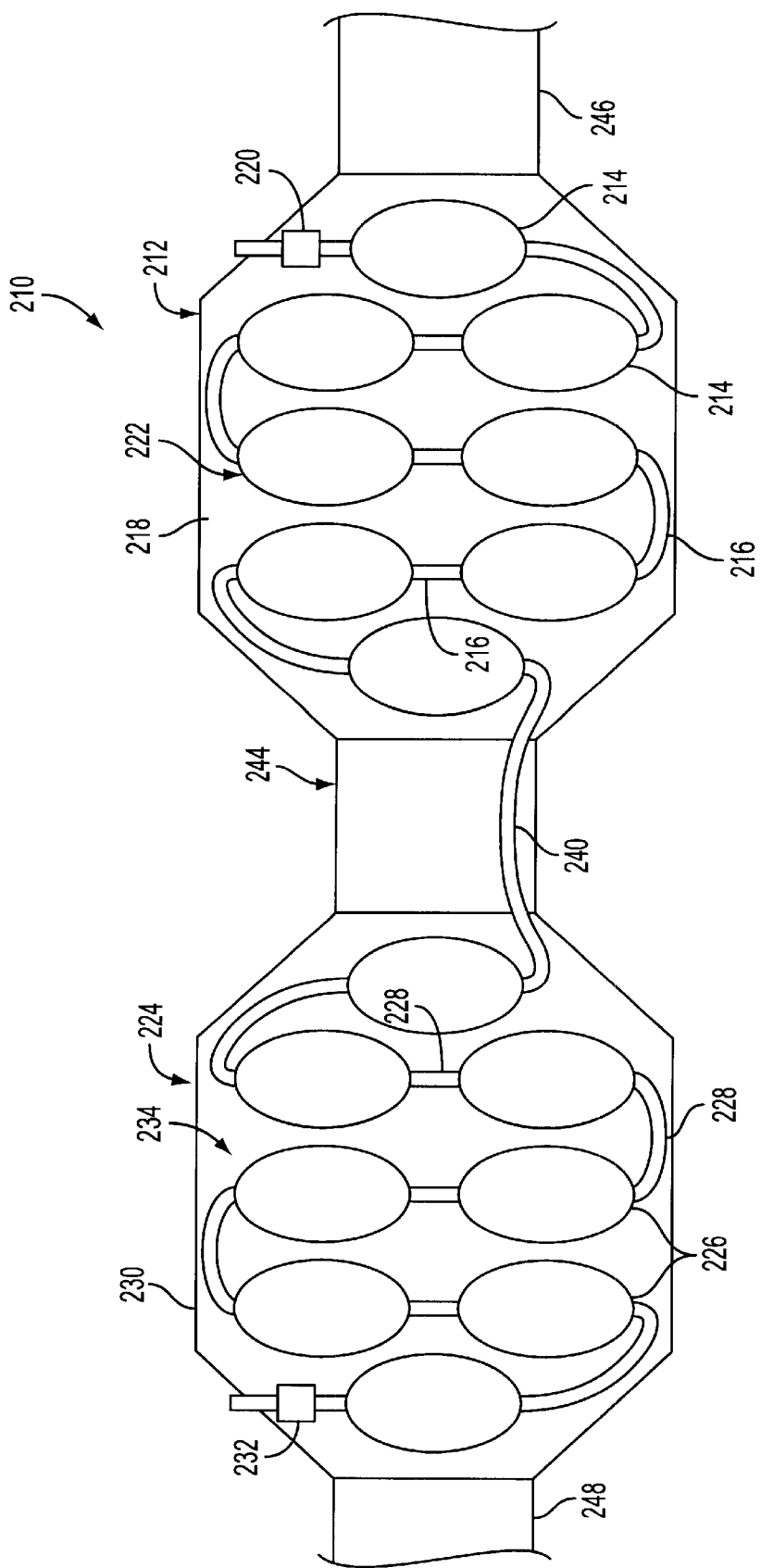
FIGS. 12 is a front elevation of a third alternative embodiment of a wearable portable pressure pack.

An alternate embodiment of a portable pressure pack incorporated into a wearable carrier garment is generally indicated by reference number 210 in FIG. 12. The wearable gas supply system 210 includes at least two pressure packs 212, 224 incorporated into a belt that may be secured around the torso of a person so as to provide a portable and ambulatory supply of fluids stored under pressure in the pressure packs 212, 224. Pressure pack 212 includes a pressure vessel 222 comprising a plurality of chambers 214 serially interconnected by conduit sections 216 of varying lengths so as to achieve the chamber arrangement desired. The pressure vessel 222 can be of the type shown in FIGS. 2 and 2A, having an internal perforated tubular core, or they can of the type shown in FIG. 4 having no internal tubular core. The chambers 214 and interconnecting conduits sections 216 are of a polymeric, filament winding-reinforced construction as described above, and the chambers 214 are preferably ellipsoidal in shape, but may be spherical.

The pressure pack 212 is encased in a padded housing 218 formed of a suitable padding material, such as neoprene. In FIG. 12, only one-half of the housing 218 is shown so as to permit viewing of the components of the pressure vessel 222. The housing 218 preferably comprises interior and posterior cushioning layers secured to one another with a suitable adhesive with the pressure vessel sandwiched therebetween. The anterior and posterior pads may each be of the egg crate type design shown in FIGS. 9 and 9A and described above, including recesses, or cavities, each conforming to one-half of the chambers 214 and the interconnecting conduit sections 216 of the pressure vessel 222. A liquid-impervious layer is preferably applied to the outer surface of the housing 218. Padded housing 218 preferably has angled corners to facilitate the comfort for the wearer by avoiding possible sharp jabs that might be inflicted by a more pointed corner. In a referred arrangement, the chambers 214 of the pressure vessel 222 are elongated ellipsoidal chambers that are sinuously arranged in a generally vertical, mutually parallel configuration as shown.

The belt 210 also includes at least a second pressure pack 224 which includes a pressure vessel 234 comprising a plurality of chambers 226 serially interconnected by interconnecting conduits sections 228 of varying lengths so as to permit the chambers to be oriented in a desired configuration. Pressure vessel 234 can be of the type shown in FIGS. 2 and 2A, having an internal perforated tubular core, or they can be of the type shown in FIG. 4 having no internal tubular core. The chambers 226 and interconnecting conduit sections 228 of the pressure vessel 234 are of a polymeric, filament winding-reinforced construction, as described above, and the chambers 226 are preferably ellipsoidal in shape, but may be spherical.

The pressure pack 224 includes a padded housing 230 that encases the pressure vessel 234. The padded housing 230 (of which only one-half is shown so as to permit viewing of the pressure vessel 234) is formed of a suitable padding material such as neoprene. The housing 230 may comprise interior and posterior cushioning layers secured to one another with a suitable adhesive with the pressure vessel 234 sandwiched therebetween. The anterior and posterior pads may each be of the egg crate type design shown in FIGS. 9 and 9A and described above.

The respective padded housings 218, 230 of the pressure packs 212, 224 are relatively rigid, so, to permit the belt 210 to conform around the torso of a wearer more easily, a flexible joint 244 is interposed between adjacent pressure packs such as pressure packs 212 and 224. A crossover line 240 interconnects the pressure vessel 222 of the pressure pack 212 and the pressure vessel 234 of the pressure pack 224. Crossover line 240 is a polymeric tubular conduit wrapped with a braided reinforcing filament fiber as described above. In a preferred construction, the tubular polymeric portion of the crossover line 240 is formed integrally with the pressure vessels 222 and 234. Crossover line 240, so as to maintain its flexibility, is not encased in a padded foam housing, but extends through a flexible sleeve connected at its opposite ends to the adjacent housings 218 and 230. Preferably, the sleeve forming the flexible joint 244 is a flexible nylon material.

Belt straps 246 and 248 are attached to the padded housings 218, 230 by any suitable means such as by attaching brackets (not shown) or by securing the ends of the straps 246 and 248 between the anterior and posterior pads of the respective housings 218 and 230. Alternatively, the straps 246, 248 could be provided as one continuous strap extending completely across the pressure packs 218, 224 and the flexible joint 244. The straps 246 and 248 include means for securing the belt 210 around the torso of a person, such as a buckle or Velcro strips.

A one-way inlet valve 220 is connected to one end of the interconnected pressure vessels 222 and 234, and a one-way outlet valve/regulator 232 is connected to an opposite end of the interconnected pressure vessels 222, 234. Both the inlet valve 220 and the outlet valve 232 are preferably vertically oriented and are disposed on an outer face of the respective housings 218, 230 and are also preferably positioned so that the respective tops thereof do not project above a top edge of the housings 218, 230. A gas delivery system, such as the gas delivery system shown in FIG. 11 and comprising a flexible tube 196, a valve regular 194, a dual lumen flexible tube 200 and a nasal cannula 204, is connected to the outlet valve 232 of the belt 210 shown in FIG. 12. Again, a breathing mask may be used instead of a nasal cannula.

While the belt 210 shown in FIG. 12 has two pressure packs 212, 224, a belt may include any number of semi-rigid pressure packs interconnected by flexible joints and having an overall length suitable for securing around the torso of a person.

While the invention has been described in connection with what are presently considered to be the most practical and preferred embodiments, it is to be understood that the invention is not to be limited to the disclosed embodiments, but, on the contrary, it is intended to cover various modifications and equivalent arrangements included within the spirit and scope of the appended claims. Thus, it is to be understood that variations in the particular parameters used in defining the present invention can be made without departing from the novel aspects of this invention as defined in the following claims.

What is claimed is:

1. A storage system for pressurized fluids comprising:
1) at least two fluid storage packs, each said fluid storage pack comprising;
   a) a pressure vessel comprising:
      i) a plurality of hollow chambers, each having a generally ellipsoidal shape;
      ii) a plurality of conduit sections, each being positioned between adjacent ones of said plurality of hollow chambers to interconnect said plurality of hollow chambers, each of said conduit sections having a maximum interior transverse dimension that is smaller than a maximum interior transverse dimension of each of said hollow chambers; and
      iii) a reinforcing filament wrapped around said hollow chambers and said conduit sections; and
   b) a housing encasing said pressure vessel and comprising:
      i) a first foam shell having a number of depressions formed therein corresponding to the number of hollow chambers comprising said pressure vessel, each of said depressions having a shape and size that correspond to approximately one half of each of said hollow chambers, adjacent ones of said depressions being connected by interconnecting channels, each of said channels having a size and shape corresponding to approximately one half of each of said conduit sections, said depressions and interconnecting channels being arranged in a preferred configuration of said plurality of chambers and conduit sections; and
      ii) a second foam shell having a number of depressions formed therein corresponding to the number of hollow chambers comprising said pressure vessel, each of said depressions having a shape and size that correspond to approximately one half of each of said hollow chambers, adjacent ones of said depressions being connected by interconnecting channels, each of said channels having a size and shape corresponding to approximately one half of each of said conduit sections, said depressions and interconnecting channels being arranged in a preferred configuration of said plurality of chambers and conduit sections, said first foam shell being arranged with said depressions and interconnecting channels thereof in opposed facing relation with respect to corresponding depressions and interconnecting channels of said second foam shell, said pressure vessel being disposed between said first and second foam shells with said plurality of hollow chambers and conduit sections being encased within mating depressions and interconnecting channels, respectively, of said first and second foam shells;
2) a flexible fluid transfer conduit connecting the pressure vessels of adjacent ones of said fluid storage packs;
3) a fluid transfer control system constructed and arranged to control flow of fluid into and out of said pressure vessels; and
4) one or more belt straps operatively coupled to said fluid storage packs and constructed and arranged to be secured around the torso of a person to provide an ambulatory supply of fluid stored in said pressure vessels.

2. A storage system for pressurized fluids comprising:
1) a least two fluid storage packs, each said fluid storage pack comprising:
   a) a pressure vessel comprising:
      i) a plurality of hollow chambers, each having a generally ellipsoidal shape;
      ii) a plurality of conduit sections, each being positioned between adjacent ones of said plurality of hollow chambers to interconnect said plurality of hollow chambers, each of said conduit sections having a maximum interior transverse dimension that is smaller than a maximum interior transverse dimension of each of said hollow chambers; and
      iii) a reinforcing filament wrapped around said hollow chambers and said conduit sections; and
   b) a housing encasing said pressure vessel; and
2) a flexible fluid transfer conduit connecting the pressure vessels of adjacent ones of said fluid storage packs;
3) a fluid transfer control system constructed and arranged to control flow of fluid into and out of said pressure vessels and comprising:
   a) a one-way inlet valve attached to one of said pressure vessels and constructed and arranged to permit fluid under pressure to be transferred trough said inlet valve and into said pressure vessels and to prevent fluid within said pressure vessels from escaping therefrom through said inlet valve; and
   b) a regulator outlet valve attached to one of said pressure vessels and being constructed and arranged to be selectively configured to either prevent fluid within said pressure vessels from escaping therefrom through said regulator outlet valve or to permit fluid within said pressure vessels to escape therefrom through said regulator outlet valve at an outlet pressure that deviates from a pressure of the fluid within said pressure vessels, wherein said housing has a generally rectangular shape with angled corners, and said inlet valve and said outlet valves are disposed at an angled corner portion of the housing of an associated pressure vessel such that no portions of said inlet and outlet valves project beyond the edges of the side portions of the housing; and 4) one or more belt straps operatively coupled to said fluid storage packs andconstructed and arranged to be secured around the torso of a person to provide an ambulatory supply of fluid stored said pressure vessels,

* * * * *